United States Patent
Gao et al.

(10) Patent No.: US 12,128,386 B2
(45) Date of Patent: Oct. 29, 2024

(54) ODH CATALYST FORMULATIONS

(71) Applicant: NOVA CHEMICALS (INTERNATIONAL) S.A., Fribourg (CH)

(72) Inventors: Xiaoliang Gao, Calgary (CA); Vasily Simanzhenkov, Calgary (CA); Leonid Kustov, Moscow (RU); Aleksey Kucherov, Moscow (RU); Elena Finashina, Moscow (RU)

(73) Assignee: NOVA Chemicals (International) S.A., Fribourg (CH)

( * ) Notice: Subject to any disclaimer, the term of this patent is extended or adjusted under 35 U.S.C. 154(b) by 429 days.

(21) Appl. No.: 17/621,001

(22) PCT Filed: Jun. 29, 2020

(86) PCT No.: PCT/IB2020/056121
§ 371 (c)(1),
(2) Date: Dec. 20, 2021

(87) PCT Pub. No.: WO2021/009588
PCT Pub. Date: Jan. 21, 2021

(65) Prior Publication Data
US 2022/0323942 A1    Oct. 13, 2022

Related U.S. Application Data

(60) Provisional application No. 62/875,742, filed on Jul. 18, 2019.

(51) Int. Cl.
*B01J 23/888* (2006.01)
*C07C 5/48* (2006.01)

(52) U.S. Cl.
CPC ............. *B01J 23/8885* (2013.01); *C07C 5/48* (2013.01); *B01J 2523/55* (2013.01);
(Continued)

(58) Field of Classification Search
CPC .................. B01J 23/8885; B01J 2523/55; B01J 2523/56; B01J 2523/64; B01J 2523/68;
(Continued)

(56) References Cited

U.S. PATENT DOCUMENTS 5,281,745 A * 1/1994 Ushikubo ............ B01J 27/0576
558/319
6,642,173 B2 * 11/2003 Bogan, Jr. ............. C07C 253/24
502/311
(Continued)

FOREIGN PATENT DOCUMENTS

EP  1123738  8/2001
WO  WO 2019/025900  2/2019

OTHER PUBLICATIONS

International Preliminary Report on Patentability in International Appln. No. PCT/IB2020/056121, mailed on Jan. 18, 2022 8 pages.
(Continued)

Primary Examiner — Patricia L. Hailey
(74) Attorney, Agent, or Firm — Fish & Richardson P.C.

(57) ABSTRACT

The oxidative dehydrogenation of ethane comprises contacting a mixture of ethane and oxygen in an ODH reactor with an ODH catalyst under conditions that promote oxidation of ethane into ethylene. Conditions within the reactor are controlled by the operator and include, but are not limited to, parameters such as 5 temperature, pressure, and flow rate. Conditions will vary and can be optimized for a specific catalyst, or whether an inert diluent is used in the mixing of the reactants. Disclosed herein is a catalyst consisting of: $Mo_{0-1}W_{0.3-1}V_{0.2-0.4}Te_{0.06-0.10}Fe_{0.0-0.10}Nb_{0.08-0.18}O_X$ where X is determined by the valance of the metals.

20 Claims, 15 Drawing Sheets

(52) U.S. Cl.
CPC ........ *B01J 2523/56* (2013.01); *B01J 2523/64* (2013.01); *B01J 2523/68* (2013.01); *B01J 2523/69* (2013.01); *B01J 2523/842* (2013.01)

(58) Field of Classification Search
CPC ...................... B01J 2523/69; B01J 2523/842; B01J 23/881; B01J 23/8877
USPC ........ 502/312, 316; 585/650, 651, 654, 662, 585/663
See application file for complete search history.

(56) References Cited

U.S. PATENT DOCUMENTS

| | | | |
|---|---|---|---|
| 6,740,620 B2 * | 5/2004 | Bogan, Jr. ............. | C07C 51/215 502/313 |
| 7,319,179 B2 | 1/2008 | Nieto et al. | |
| 2002/0183198 A1 * | 12/2002 | Gaffney ................ | C07C 51/252 502/215 |
| 2003/0004379 A1 * | 1/2003 | Gaffney .................. | B01J 23/18 502/215 |
| 2004/0063990 A1 * | 4/2004 | Gaffney ................ | C07C 51/215 502/212 |
| 2020/0290026 A1 * | 9/2020 | Mestl .................... | C07C 5/3332 |

OTHER PUBLICATIONS

International Search Report and Written Opinion in International Appln. No. PCT/IB2020/056121, mailed on Sep. 22, 2020, 11 pages.

O'Connor et al., "Application of the Rietveld Refinement Procedure in Assaying Powdered Mixtures," Powder Diffraction, Mar. 1988, 3(1):2-6.

* cited by examiner

ODH CATALYST FORMULATIONS

CROSS-REFERENCE TO RELATED APPLICATION

This application is a National Stage Application under 35 U.S.C. § 371 and claims the benefit of International Application No. PCT/IB2020/056121, filed Jun. 29, 2020, which claims priority to U.S. Ser. No. 62/875,742, filed on Jul. 18, 2019. The disclosure of the prior applications is considered part of and is incorporated by reference in the disclosure of this application.

TECHNICAL FIELD

The present disclosure relates to catalysts for the oxidative dehydrogenation of ethane to ethylene in the presence of a continuous flow of an oxidant such as air or synthetic air at temperatures from 300° C. to 450° C. in the presence of a catalyst that includes $Mo_{0-1}W_{0.3-1}V_{0.2-0.4}Te_{0.06-0.10}Fe_{0.0-0.10}Nb_{0.08-0.18}O_X$ where X is determined by the valance of the metal oxides.

BACKGROUND ART

The oxidative dehydrogenation of ethane includes contacting a mixture of ethane and oxygen in an ODH reactor with an ODH catalyst under conditions that promote oxidation of ethane into ethylene. Conditions within the reactor are controlled by the operator and include, but are not limited to, parameters such as temperature, pressure, and flow rate. Conditions will vary and can be optimized for a specific catalyst, or whether an inert diluent is used in the mixing of the reactants.

It is known that oxidative dehydrogenation can be used to convert alkanes to alkenes, in particular ethane to ethylene. It is also known by persons skilled in the art that certain catalysts can be used to perform the oxidative dehydrogenation of ethane to ethylene. Accordingly, an ODH catalyst including $Mo_{0-1}W_{0.3-1}V_{0.2-0.4}Te_{0.06-0.10}Fe_{0.0-0.10}Nb_{0.08-0.18}O_X$, where X is determined by the valance of the metal oxides, for converting ethane to ethylene in an ODH reactor is disclosed.

SUMMARY OF INVENTION

An embodiment of the disclosure provides a catalyst that includes $Mo_{0-1}W_{0.3-1}V_{0.2-0.4}Te_{0.06-0.10}Fe_{0.0-0.10}Nb_{0.08-0.18}O_X$ where X is determined by the valance of the metals.

In a further embodiment, the catalyst includes $Mo_{0.3-0.8}W_{0.3-0.8}V_{0.2-0.4}Te_{0.06-0.10}Fe_{0.06-0.10}Nb_{0.08-0.14}O_X$ where X is determined by the valance of the metals.

In a further embodiment, the catalyst includes $Mo_{0.45-0.55}W_{0.45-0.55}V_{0.25-0.35}Te_{0.07-0.09}Fe_{0.07-0.09}Nb_{0.11-0.13}O_X$ where X is determined by the valance of the metals.

In a further embodiment, the catalyst includes $Mo_{0.48-0.52}W_{0.48-0.52}V_{0.28-0.32}Te_{0.075-0.085}Fe_{0.075-0.085}Nb_{0.115-0.125}O_X$ where X is determined by the valance of the metals.

In a further embodiment, the catalyst has been treated with the equivalent of from 0.3 mL to 2.8 mL, in some embodiments from 0.3 mL to 2.5 mL of a 30 wt. % solution of aqueous $H_2O_2$ per gram of catalyst precursor prior to or subsequent to calcination. In a further embodiment, the catalyst is supported on a support chosen from oxides of titanium, zirconia, aluminum, niobium, magnesium, yttrium, lanthanum, silicon, zeolites and clays and mixtures thereof.

In a further embodiment, the catalyst has a conversion from 65% to 90% for the oxidative dehydrogenation of ethane to ethylene at temperatures from 300° C. to 450° C.

In a further embodiment, the catalyst has a conversion from 65% to 85% for the oxidative dehydrogenation of ethane to ethylene at temperatures from 350° C. to 425° C.

In a further embodiment, the catalyst is prepared by a hydrothermal process at a pressure from 10 psi to 190 psi (960 kPa to 1300 kPa).

In a further embodiment, the catalyst is prepared by a hydrothermal process at a pressure from up to 10 psig (68.9 kPag) for a period of time not less than 21 hours.

In a further embodiment, the catalyst is prepared by a hydrothermal process at a pressure from up to 10 psig (68.9 kPag) for a period of time less than 75 hours.

In a further embodiment, the catalyst is prepared by a hydrothermal process at a pressure from up to 10 psig (68.9 kPag) for a period of time from 22 to 73 hours.

In a further embodiment, the catalyst is prepared by a hydrothermal process with agitation and simultaneous removal of gaseous byproduct species produced during the reaction, at a pressure from 1 to 8 psig (6.89 kPag to 55.1 kPag).

In a further embodiment, the catalyst is prepared by a hydrothermal process with agitation and simultaneous removal of gaseous byproduct species produced during the reaction, at a pressure less than 5 psig (34.4 kPag) above atmospheric pressure.

DESCRIPTION OF EMBODIMENTS

Numbers Ranges

Figure 1:
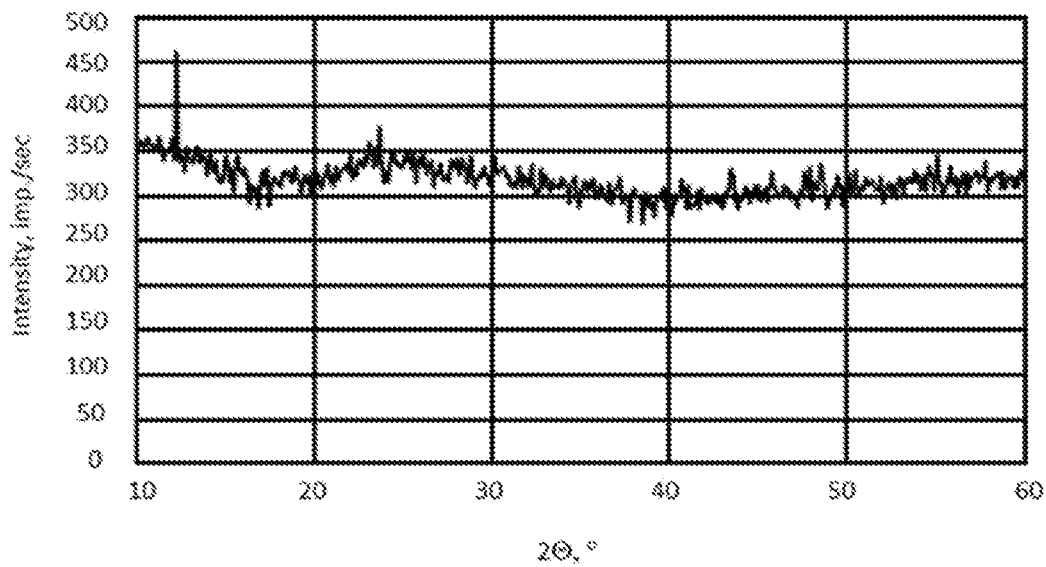
FIG. 1 is a plot of the X-Ray Diffraction of the catalyst of Example 1.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components used will conform to the maximum of 100 percent.

In the specification the phrase "the temperature at which there is 25% conversion of ethane to ethylene" is determined by plotting a graph of conversion to ethylene against temperature typically with data points below and above 25% conversion or the data is fit to an equation and the temperature at which there is a 25% conversion of ethane to ethylene is determined. In some instances, in the examples the data had to be extrapolated to determine the temperature at which 25% conversion occurred.

In the specification the phrase "selectivity at 25% conversion" is determined by plotting the selectivity as function of temperature or fit to an equation. Then having calculated the temperature at which 25% conversion occurs one can determine either from the graph or from the equation the selectivity at that temperature.

The ratio of amorphous component to crystalline component may be determined by obtaining an X-ray Powder Diffraction (XRD) for the calcined catalyst. Within 24 hours of obtaining the sample XRD, a standard (100% crystalline) material such as Corundum is run on the XRD instrument to determine the K factor for the instrument. Then, knowing the K factor, the percentage of crystalline phase per unit mass of sample is determined and the difference is the weight of the amorphous content per unit mass of sample. Such a technique is disclosed in: O'Connor and Raven (1988), Powder Diffraction, 3(1), 2-6.

A typical procedure is as follows:

1. The sample is finely ground to reduce particle size to less than 250 microns and obtain a uniform mixture.

2. The ground sample is loaded onto an XRD sample holder preferably having an Energy Dispersive X-ray Spectroscopy (EDS) stub for XRD and EDS analysis.

3. Acquire the XRD spectrum and where applicable perform EDS analysis using a scanning electron microscope (SEM).

4. Combine Highscore Plus, EDS and Rietveld Refinement to perform qualitative and quantitative analysis.

5. Amorphous analysis—Run standard using exactly same holder and same program as with the sample. Standard must be run within 24 hours after the sample was run.

6. Use external standard method to determine the amorphous content.

7. With an external standard method, determine an instrument intensity constant often called K-factor (sometimes called G-factor as well). Instrument and software should already have program set up for this method.

8. Generate report.

The Catalyst

The catalyst of the present disclosure includes $Mo_{0-1}W_{0.3-1}V_{0.2-0.4}Te_{0.06-0.10}Fe_{0.0-0.10}Nb_{0.08.18}O_X$, where X is determined by the valance of the metal oxides. In some embodiments, the catalyst includes $Mo_{0.3-0.8}W_{0.3-0.8}V_{0.2-0.4}Te_{0.06-0.10}Fe_{0.06-0.10}Nb_{0.08-6.14}O_X$ where X is determined by the valance of the metal oxides. In some embodiments, the catalyst includes $Mo_{0.45-0.55}W_{0.45-0.55}V_{0.25-0.35}Te_{0.07-0.09}Fe_{0.07-0.09}Nb_{0.11-0.13}O_X$ where X is determined by the valance of the metal oxides. In further embodiments, the catalyst includes $Mo_{0.48-0.52}W_{0.48-0.52}V_{0.28-0.32}Te_{0.075-0.085}Fe_{0.075-0.085}Nb_{0.115-0.125}O_X$ where X is determined by the valance of the metal oxides.

The Catalyst Precursor

The catalyst precursor may be prepared using a hydrothermal process including following these steps (in the following procedure the molar ratios are based on the final catalyst product):

i) Forming an aqueous solution of ammonium heptamolybdate (tetrahydrate), ammonium metatungstate hydrate ((NH$_4$)6H$_2$W$_{12}$O$_{40}$.2.3H$_2$O), and telluric acid, and optionally Fe(NO$_3$)$_3$.9H$_2$O or a comparable water soluble salt of iron in a molar ratio of Mo 0.3 to 0.8:W 0.3-0.8:Te 0.06-0.1:Fe 0.00 to 0.10, at a temperature from 30° C. to 85° C. and adjusting the pH of the solution to 6.5 to 8.5, such as 7 to 8, or such as from 7.3 to 7.7 optionally with a nitrogen-containing base to form soluble salts of the metals.

ii) Stirring the pH adjusted solution for a time of not less than 15 minutes, in some instances from not less than 2 hours, in some instances not more than 4 hours.

iii) Adjusting the pH of the resulting solution to from 4.5 to 5.5, such as 4.8 to 5.2, or from 5.0 to 5.2 with an acid, such as sulfuric acid (0.01-18 M, typically 2-18 M) and stirring the resulting solution at a temperature of 80° C. until it is homogeneous in some instances with a stirring time up to 30 minutes. In some circumstances, to maintain 80° C. temperature, a cooling device needs to be used to maintain temperature at 80° C.

iv) Preparing an aqueous solution of vanadyl sulphate at a temperature from room temperature to 80° C. (such as from 50° C. to 70° C., or from 55° C. to 65° C.).

v) Mixing the solutions from steps i) and iv) together to provide a molar ratio of V:Mo from 0.2-0.4 to 0.3-0.8.

vi) Preparing a solution of H$_2$O$_2$O$_4$ and Nb$_2$O$_5$.xH$_2$O in a molar ratio from 5.0 to 6:1, in some instances 5.0-5.3:1.

vii) Slowly (dropwise) adding the solution from step vi) to the solution of step vi) to provide molar ratio of Nb:Mo from 0.06 to 0.10:0.3 to 0.8 to form a slurry (typically the addition is at temperatures from 20° C. and 80° C.; such as from 20° C. to 30° C.).

viii) Heating the resulting slurry in an autoclave under an inert gas, air, carbon dioxide, carbon monoxide and mixtures thereof at a pressure of not less than 1 psig and at a temperature from 140° C. to 190° C. for not less than 6 hours, typically not less than 6 hours.

The temperature for the hydrothermal treatment may range from 140° C. to 180° C., in some embodiments from 145° C. to 175° C.

The pressure in the autoclave may range from equal or above the saturated water vapor pressure at the corresponding reaction temperature in some embodiments from 1 to 8 psig (6.89 kPag to 55.1 kPag), such as less than 5 psig (34.4 kPag); in other embodiments from 30 to 200 psig (206 kPag to 1375 kPag), in some embodiments from 55 psig (380 kPag) to 170 psig (1170 kPag) above atmospheric pressure.

The gaseous product species is vented from the autoclave (reactor).

Optionally, there is a condenser upstream of the autoclave outlet which may be operated at a temperature above 0° C. and below reaction temperature.

The pressure inside the autoclave may be maintained above atmospheric using a liquid filled column or bubbler or a pressure regulator valve.

The hydrothermal treatment may be from 6 to 15 hours.

The autoclave (reactor) is allowed to cool to room temperature, typically overnight. The reactor contents are filtered using a Buchner filter and washed with distilled water or an aqueous oxalic acid solution and dried in an oven for not less than 6 hours at a temperature from 70° C. to 120° C.

In some embodiments, the precatalyst is separated from the aqueous phase, typically by filtration or evaporation, and washed with distilled or deionized water and dried in an oven for not less than 6 hours at a temperature from 70° C. to 120° C. The precatalyst may be dried in an atmosphere of substantially one or more inert gases. In some instances, optionally the dried precatalyst may be ground using mechanical means (e.g., a ball or roller mill) or the dried precatalyst could be subject to cryogenic grinding. The dried and ground precatalyst may in some instances be subject to sieving through a small particle size sieve to obtain a fraction having a particle size less than 250 microns, such as less than 125 microns.

In some embodiments the product from the hydrothermal treatment is treated with from 0.3 to 2.5 mL of a 30 wt. % solution of aqueous H$_2$O$_2$ per gram of catalyst precursor.

Calcination

The precatalyst is then subjected to calcination in an inert gas (e.g., less than 0.05, in some instances less than 0.03 in some instances less than 0.01 vol % of O$_2$), typically at temperatures greater than 350° C., such as greater than 500° C., or above 600° C. but below temperatures where some of the metallic components of the catalyst may sublimate (e.g., Te) typically below about 900° C.

In an alternative embodiment, the catalyst precursor is calcined in an inert container with a flow passage there through, comprising heating the catalyst precursor at a rate from 0.5 to 10° C. per minute, in some embodiments from 0.9 to 2° C. per min, from room temperature to a temperature from 300° C. to 540° C., in some cases from 400° C. to 525° C., under a dynamic stream of inert gas such as nitrogen, helium, etc. and mixtures thereof, a flow rate of the inert gas comparable to a flow of nitrogen through a 1 inch internal diameter tube having a length of 152 cm (59.8 inches) at a flow rate from 200-500 sccm per 30-250 gram of catalyst precursor.

The inert container may have a heat conductivity greater than 0.34 Wm$^{-1}$·K$^{-1}$, in some embodiments from 1.2 Wm$^{-1}$·K$^{-1}$ to 50 Wm$^{-1}$·K$^{-1}$. The container may be made from high temperature glass (e.g., Pyrex), quartz, ceramic (e.g., Beryllium Oxide), alumina or steel (such as a low carbon steel or a grade of stainless steel).

The inert gas (e.g., nitrogen) in the calcination chamber is not static. It is dynamic and flows over the precatalyst. Flow rates are a function of many variables such as the shape of the chamber, the size of the opening and exit ports of the chamber, the pressure drop across the inlets and outlets. One skilled in the art or having access to computational fluid dynamic programs can calculate flow rates. However, some starting point for the calculation is required. A starting point is the flow rate for a tubular drying chamber, or tube, having a one inch (2.54 cm) internal diameter and a length of 152 cm (59.8 inches) is from 200 to 500 sccm per 30 to 250 grams of catalyst precursor. In some instances, the flow rate may be equivalent to a flow rate through a 1 inch diameter tubular drying chamber having a length of 152 cm from 250 to 450 sccm per 30 to 250 grams of catalyst precursor. However, the flow rate needs to be increased as the chamber volume increases.

The pressure in the interior of the flow chamber should be at least 1 psig (6.9 kPag) in some instances from 1 to 5 psig, in some cases, higher than 5 psig.

The temperature of the gas flowing through the chamber is from 300° C. to 540° C. (in some cases from 400° C. to 525° C.). The temperature of the inert gas flowing over the catalyst is influenced by the temperature of the calcination and the flow rate. The catalyst precursor is held at the calcining temperature for at least 2 hours, typically from 2 to 24 hours, and cooled to room temperature.

During the calcining process the catalyst precursor is at least partially enclosed in a breathable or permeable covering. In some embodiments, it is preferred that the covering substantially encloses the catalyst precursor (e.g., at least 50% and optionally not less than 75% of the external surface of the catalyst precursor is covered by the breathable or permeable covering). The covering should have a permeability to gas from 5 cubic feet per minute (8.5 cubic meter/h) to 100 cubic feet per minute (170 cubic meter/hour) in some cases from 10 cubic feet per minute to 60 cubic feet per minute according to the measurement method specified by ASTM E2945-14. The permeable covering should have a melting point greater than 600° C. Provided the covering is breathable or permeable, it may be a woven or nonwoven material. For example, it could be a plastic or metallic (or a metalized plastic substrate) substrate having a melting point above 600° C. Permeability could be provided by any mechanical means to permit the passage of gas through the covering such as needle type punching process. The permeable covering could be a non-woven chosen from polymers having a melting point above 600° C. and glass and mineral fiber, such as glass and mineral fiber (e.g., fiber glass batting). If the covering is a woven fabric, the permeability would be controlled by the tightness of the weaving of the fabric. For example, the fabric could have up to 960 of pores per $cm^2$ for multifilament woven fabric.

In some embodiments, activated carbon (greater than 90%, such as greater than 95% purity) may be placed on top of the permeable covering to scavenge oxygen and materials released from the catalyst. The carbon may be used in amounts up to 0.5 g, typically 0.1 to 0.3 g per 1 g of catalyst precursor being calcined.

Binder Support

In some embodiments, from 10 to 95, such as from 25 to 80, or for example from 30 to 45, weight % of the catalyst is bound, agglomerated, filled, promoted, impregnated, or supported with from 5 to 90, such as from 20 to 75, or for example from 55 to 70 weight % of a material (for example, a binder) other than active phase chosen from acidic, basic or neutral binder slurries of $TiO_2$, $ZrO_2$ $Al_2O_3$, $AlO(OH)$, $Nb_2O_5$, $FeO(OH)$ and mixtures thereof provided that $ZrO_2$ is not used in combination with an aluminum containing binder.

The ODH Process

The oxidative dehydrogenation of ethane comprises contacting a mixture of ethane and oxygen in an ODH reactor with an ODH catalyst under conditions that promote oxidation of ethane into ethylene. Conditions within the reactor are controlled by the operator and include, but are not limited to, parameters such as temperature, pressure, and flow rate. Conditions will vary and can be optimized for a specific catalyst, or whether an inert diluent is used in the mixing of the reactants.

Use of an ODH reactor for performing an ODH process consistent with the present disclosure falls within the knowledge of the person skilled in the art. The oxidative dehydrogenation of ethane to ethylene may be conducted at temperatures from 300° C. to 450° C., typically from 300° C. to 425° C., such as from 330° C. to 400° C., at pressures from 0.5 to 100 psi (3.447 to 689.47 kPa), or, for example, from 15 to 50 psi (103.4 to 344.73 kPa), and the residence time of ethane in the reactor is typically from 0.002 to 30 seconds, such as from 1 to 10 seconds.

The process has a selectivity for ethylene in the range from 65% to 85%, such as, greater than 70%, or, for example, greater than 75%. The flow of reactants and inert diluent can be described in any number of ways known in the art. Typically, flow is described and measured in relation to the volume of all feed gases (reactants and diluent) that pass over the volume of the active catalyst bed in one hour, or gas hourly space velocity (GHSV). The GHSV can range from 500 to 30000 $h^{-1}$, such as greater than 1000 $h^{-1}$. The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include diluents added to the gas mixture. When including the weight of diluents, when used, the WHSV may range from 0.5 $h^{-1}$ to 50 $h^{-1}$, such as from 1.0 to 25.0 $h^{-1}$.

The flow of gases through the reactor may also be described as the linear velocity of the gas stream (m/s), which is defined in the art as the flow rate of the gas stream/cross-sectional surface area of the reactor/void fraction of the catalyst bed. The flow rate generally means the total of the flow rates of all the gases entering the reactor, and is measured where the oxygen and alkane first contact the catalyst and at the temperature and pressure at that point. The cross-section of the reactor is also measured at the entrance of the catalyst bed. The void fraction of the catalyst bed is defined as the volume of voids in the catalyst bed/total volume of the catalyst bed. The volume of voids refers to the voids between catalyst particles and does not include the volume of pores inside the catalyst particles. The linear velocity can range from 5 cm/sec to 1500 cm/sec, such as from 10 cm/sec to 500 cm/sec.

The space-time yield of ethylene (or catalyst productivity) in g/hour per kg of the catalyst should be not less than 900, such as greater than 1500, or greater than 3000, or, for example, greater than 3500 at 350° C. to 400° C. It should be noted that the productivity of the catalyst will increase with increasing temperature until the selectivity is sacrificed.

ODH Reactor

The present disclosure contemplates the use of any of the known reactor types applicable for the ODH of ethane. Particularly suited for use in the present disclosure are conventional fixed bed reactors. In a typical fixed bed reactor, reactants are introduced into the reactor at one end, flow past an immobilized catalyst, products are formed and leave at the other end of the reactor. Designing a fixed bed reactor suitable can follow techniques known for reactors of this type. A person skilled in the art would know which features are required with respect to shape and dimensions, inputs for reactants, outputs for products, temperature and pressure control, and means for immobilizing the catalyst.

The present disclosure also contemplates the use of inert non-catalytic heat dissipative particles within one or more of the ODH reactors. The heat dissipative particles are present within the bed and comprise one or more non catalytic inert particulates having a melting point at least 30° C., in some embodiments at least 250° C., in further embodiments at least 500° C. above the temperature upper control limit for the reaction, a particle size in range of 0.5 mm to 75 mm, in some embodiments 0.5 mm to 15 mm, in further embodiments in range of 0.5 mm to 8 mm, such as in the range of 0.5 mm to 5 mm and a thermal conductivity of greater than 30 W/mK (watts/meter Kelvin) within the reaction temperature control limits. In some embodiments the particulates are metals alloys and compounds having a thermal conductivity of greater than 50 W/mK (watts/meter Kelvin) within the reaction temperature control limits. Some suitable metals include silver, copper, gold, aluminum, steel, stainless steel, molybdenum, and tungsten.

The heat dissipative particles may have a particle size typically from about 1 mm to 15 mm. In some embodiments the particle size may be from about 1 mm to about 8 mm. The heat dissipative particles may be added to the fixed bed in an amount from 5 wt. % to 95 wt. %, in some embodiments 30 wt. % to 70 wt. %, in other embodiments 45 wt. % to 60 wt. % based on the entire weight of the fixed bed.

The particles are employed to potentially improve cooling homogeneity and reduction of hot spots in the fixed bed by transferring heat directly to the walls of the reactor.

Also contemplated by the present disclosure is the use of a fluidized bed reactor. These types of reactors are also well known. Typically, the catalyst is supported by a porous structure, or distributor plate, located near a bottom end of the reactor and reactants flow through at a velocity sufficient to fluidize the bed (the catalyst rises and begins to swirl around in a fluidized manner). The reactants are converted to products upon contact with the fluidized catalyst and subsequently removed from the upper end of the reactor. Design considerations include shape of the reactor and distributor plate, input and output, and temperature and pressure control, all of which would fall under knowledge of the person skilled in the art.

The present disclosure also embodies using a combination of both fixed bed and fluidized bed reactors, each with the same or different catalyst. The multiple reactors may be in series, or parallel configuration, design of which falls within the knowledge of the worker skilled in the art.

Flammability Limits

The safety of the process is a primary concern. For that reason, mixtures of ethane with oxygen should preferably include ratios that fall outside of the flammability envelope. In this instance, the percentage of oxygen in the mixture is not greater than 30%, such as not greater than 25%, or, for example, not greater than 20%. While a person skilled in the art would be able to determine an appropriate level, it is recommended that the percentage of ethane not exceed 40%. For instances where the mixture of gases prior to ODH comprises 20% oxygen and 40% ethane, the balance must be made up with an inert diluent, such as one or more of nitrogen, carbon dioxide, and steam. The inert diluent should exist in the gaseous state in the conditions within the reactor and should not increase the flammability of the hydrocarbon added to the reactor, characteristics that a skilled worker would understand when deciding on which inert diluent to employ. Inert diluent can be added to either of the ethane or the oxygen containing gas prior to entering the ODH reactor or may be added directly into the ODH reactor.

Feed mixtures that fall within the flammability envelope are not ideal but may be employed in instances where the mixture exists in conditions that prevent propagation of an explosive event. That is, the flammable mixture is created within a medium where ignition is immediately quenched. For example, a user may design a reactor where oxygen and the ethane are mixed at a point where they are surrounded by flame arresting material. Any ignition would be quenched by the surrounding material. Flame arresting materials include but is not limited to non-flammable liquids (e.g., water), metallic or ceramic components, such as stainless-steel walls or ceramic supports. Another possibility is to mix oxygen and ethane at a low temperature, where an ignition event would not lead to an explosion, then introduce into the reactor before increasing the temperature. The flammable conditions don't exist until the mixture is surrounded by the flame arrestor material inside of the reactor.

Steam may be added to the feed to the reactor or directly to the reactor. The addition of steam tends to reduce the production of $CO_2$. At temperatures ranging from 300° C. to 340° C. the carbon dioxide selectivity may change from 1 wt. % to 20 wt. %, depending upon the change in steam added to the reaction. At higher temperatures, ranging from 350° C. to 425° C., the change in carbon dioxide selectivity ranges from 0.25 wt. % to 1.5 wt. %. At reaction temperatures less than 340° C., changing the amount of steam added to the reactor by at least 20 wt. % results in a change in carbon dioxide output, measured as normalized product selectivity, of at least 1 wt. %. When reaction temperatures are greater than 350° C., changing the amount of steam added to the reactor by at least 20 wt. %, results in a change in carbon dioxide selectivity of at least 0.25 wt. %.

Downstream Purification and Separation

Generally, the ODH of ethane results in a product stream that includes unreacted ethane, ethylene, water and one or more of carbon dioxide, acetic acid, and carbon monoxide. The variety of products necessitates separation downstream of the reactor. Acetic acid and water are removed using a quench tower, while carbon dioxide can be removed via a combination of an amine wash tower and a caustic tower. The remaining ethane and ethylene can be separated using a splitter so that the ethane can be recycled to the ODH reactor and the relatively pure ethylene can be used in downstream applications, most notably polymerization using any known catalyst to make polyethylene. For example, the ethylene produced can be used to make low density polyethylene (LDPE), linear low density polyethylene (LLDPE), high density polyethylene (HDPE), and the lowest density products, elastomers and plastomers, using methods known in the art. If acetic acid is produced, the ethylene and acetic acid could be reacted to produce vinyl acetate monomer.

The carbon dioxide removed by the amine wash tower would normally be flared off, contributing to the emission of greenhouse gases.

An embodiment of the disclosure provides a catalyst that includes $Mo_{0-1}W_{0.3-1}V_{0.2-0.4}Te_{0.06-0.10}Fe_{0.0-0.10}Nb_{0.08.18}O_X$ where X is determined by the valance of the metals. In further embodiments, the catalyst includes $Mo_{0.3-0.8}W_{0.3-0.8}V_{0.2-0.4}Te_{0.06-0.10}Fe_{0.06-0.10}Nb_{0.08-014}O_X$. In some embodiments, the catalyst includes $Mo_{0.45-0.55}W_{0.45-0.55}V_{0.25-0.35}Te_{0.07-0.09}Fe_{0.07-0.09}Nb_{0.11-0.13}O_X$. In some embodiments, the catalyst includes $Mo_{0.48-0.52}W_{0.48-0.52}V_{0.28-0.32}Te_{0.075-0.085}Fe_{0.075-0.085}Nb_{0.115-0.125}O_X$ where in each case X is determined by the valance of the metals.

In a further embodiment, the catalyst has been treated with the equivalent of from 0.3 mL to 2.8 mL, in some embodiments from 0.3 mL to 2.5 mL of a 30 wt. % solution of aqueous $H_2O_2$ per gram of catalyst precursor prior to or subsequent to calcination.

In a further embodiment, the catalyst is supported on a support chosen from oxides of titanium, zirconia, aluminum, niobium, magnesium, yttrium, lanthanum, silicon, zeolites and clays and mixtures thereof.

In further embodiments, the catalyst has a conversion from 65% to 90% for the oxidative dehydrogenation of ethane to ethylene at temperatures from 300° C. to 450° C. In further embodiments, the catalyst has a conversion from 65% to 85% for the oxidative dehydrogenation of ethane to ethylene at temperatures from 350° C. to 425° C.

In further embodiments, the catalyst is prepared by a hydrothermal process at a pressure from 10 psi to 190 psi (960 kPa to 1300 kPa). In further embodiments, the catalyst is prepared by a hydrothermal process at a pressure from up to 10 psig (68.9 kPag) for a period of time not less than 21 hours. In further embodiments, the catalyst is prepared by a hydrothermal process at a pressure from up to 10 psig (68.9 kPag) for a period of time less than 75 hours. In further embodiments, the catalyst is prepared by a hydrothermal process at a pressure from up to 10 psig (68.9 kPag) for a period of time from 22 to 73 hours.

In further embodiments, the catalyst is prepared by a hydrothermal process with agitation and simultaneous removal of gaseous byproduct species produced during the reaction, at a pressure from 1 to 8 psig (6.89 kPag to 55.1 kPag). In further embodiments, the catalyst is prepared by a hydrothermal process with agitation and simultaneous removal of gaseous byproduct species produced during the reaction, at a pressure less than 5 psig (34.4 kPag) above atmospheric pressure.

EXAMPLES

The present disclosure will now be illustrated by the following non-limiting examples.

Example 1

Catalyst Preparation: $(NH_4)_6H_2W_{12}O_{40} \cdot 2.3H_2O$ or $(NH_4)_6Mo_7O_{24} \cdot 4H_2O$ was dissolved in 20 mL of deionized water at room temperature and then telluric acid ($H_6TeO_6$) or $Fe(NO_3)_3 \cdot 9H_2O$ or $Sb_2(SO_4)_3$ was added to the solution obtained and stirred to produce clear solution (solution 1) or yellow if Fe was used. $VOSO_4 \cdot H_2O$ was dissolved in 10 mL of distilled water in a 50 mL beaker at room temperature. The $VOSO_4$ solution was poured into solution 1 and a brown solution resulted immediately. The resulting dark brown solution was stirred under air atmosphere for 5 minutes (solution 2). $H_3[NbO(C_2O_4)_3] \cdot 7.5\ H_2O$ was dissolved (suspended) in 10 mL of warm water (~80° C.) and added dropwise under air atmosphere to the solution 2. A colored slurry formed, which was stirred for 10 minutes under air atmosphere.

Hydrothermal Treatment Step: The slurries were transferred into a steel autoclaves with glass or Teflon liners. Pure nitrogen was bubbled via each liner containing by glass capillary for 5 minutes. The autoclaves were closed and put into an oven and heated to 175° C. and the reaction was let to proceed for 48 hours.

After 48 hours, the oven was turned off and the reactors and contents were allowed to cool down to room temperature slowly. The solids obtained were filtered, rinsed with approximately 1,000 mL (each sample) of distilled water and were dried in an oven at 90° C. overnight to produce crude ODH catalysts.

Calcination Step: The dried catalyst precursors were grinded into powder using a mortar/pestle. Catalyst precursor material was loaded in a quartz boat and the boat was placed into glass furnace tube which is used for calcination. The setup was purge under purified nitrogen flow (<0.3 ppm $O_2$) and then the heating program on the furnace was started (room temperature to 600° C. in 6 hours, held at 600° C. for 2 hours). The calcination proceeded under a slow stream (30 mL/min) of purified nitrogen (vent through silicone oil bubbler). The solid obtained was a black powder, which was ground, mold in tablet and ground again and then sieved to collect the fraction 0.8 mm to 1.0 mm resulting in final catalysts which were tested for activity and selectivity.

The resulting catalysts were tested for the oxidative dehydrogenation of a feed comprising 76 vol % $C_2H_6$ and 24 vol % oxygen at a flow rate of 600 cm³ per hour over a range of temperatures to determine the conversion (oxygen ethane and to ethylene), the selectivity to ethylene and the conversion in mol/hr per gram of catalyst.

XRD diffraction patterns were obtained for a number of samples which were consistent with XRD diffraction patterns for $Mo_1V_{0.3}Te_{0.08}Nb_{0.12}O_X$ mixed metal oxide such as FIG. 1 of U.S. Pat. No. 7,319,179 issued Jan. 15, 2008 in the name of Lopez Nieto et al.

Sample preparation of the four-component catalyst (BuMo)TeVNbO was as follows. Preparation of tetrabutyl ammonium molybdate $(Bu_4N)_2MoO_4$: Solution of tetrabutyl ammonium bromide (~0.5 M) in water was passed through glass column with base anion exchange resin and solution of tetrabutyl ammonium hydroxide was obtained. This solution was mixed with excess of molybdenum acid ($H_2MoO_4$). Resulting solution was filtered from unreacted molybdenum acid and rotary evaporated under gentle heating. White powder obtained was re-dissolved in EtOH, solution was filtered, evaporated and powder obtained was dried at 80° C. overnight. This powder was used as molybdenum source for slurry preparation.

$(Bu_4N)_2MoO_4$ was suspended in 20 mL of deionized water at room temperature and then $H_6TeO_6$ was added to the suspension obtained and stirred for 10 minutes. $VOSO_4 \cdot H_2O$ was dissolved in 10 mL of distilled water in a 50 mL beaker at room temperature. The $VOSO_4$ solution was poured into the suspension and a brown slurry resulted immediately. The resulting dark brown slurry was stirred under air atmosphere for 5 minutes. $H_3[NbO(C_2O_4)_3] \cdot 7.5\ H_2O$ was dissolved (suspended) in 10 mL of warm water (~80° C.) and added dropwise under air atmosphere to the slurry, which was stirred for 10 minutes under air atmosphere. The catalyst was calcined.

FIG. 1 is the XRD of the resulting catalyst. The X-ray Diffraction (XRD) pattern of this sample of catalyst is significantly different from the XRD for example of FIG. 1 of U.S. Pat. No. 7,319,179 issued Jan. 15, 2008 in the name of Lopez Nieto et al.

Figure 2:
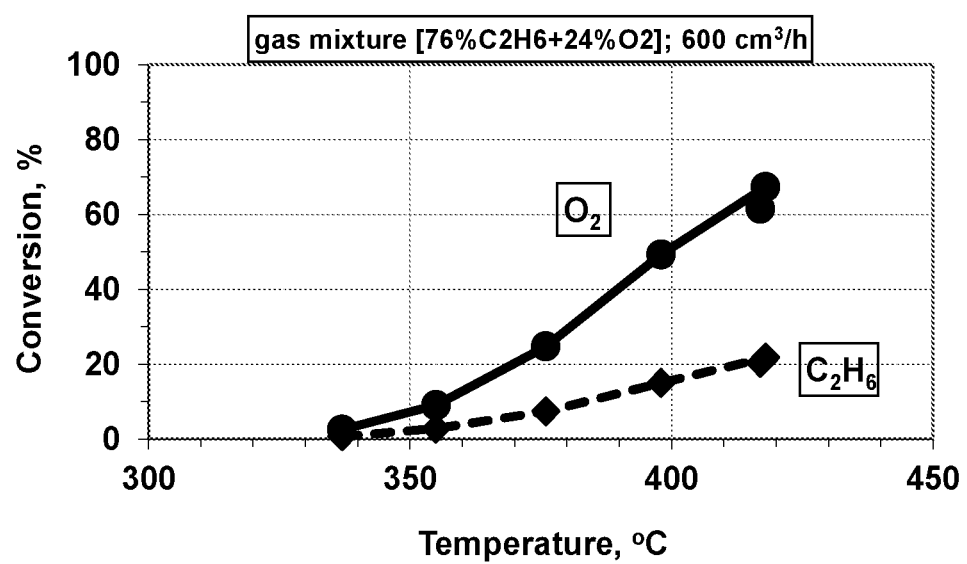
FIG. 2 is a plot of the conversion of the catalyst of Example 1.
Figure 3:
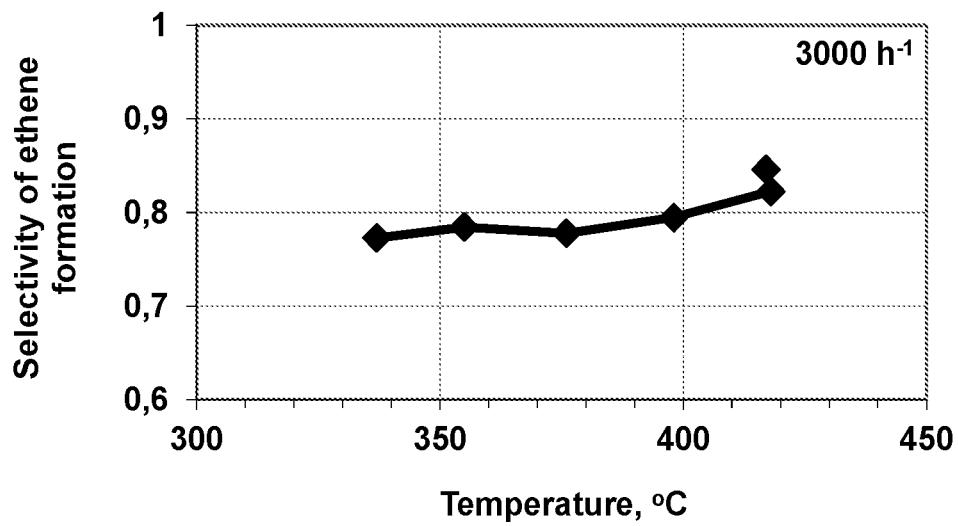
FIG. 3 is a plot of the selectivity of the catalyst of Example 1.

FIG. 2 is a plot of the conversion and FIG. 3 is a plot of the selectivity of the sample under the conditions outlined above. The approach used seems not to be promising as activity of the catalyst prepared from the modified Mo-precursor is quite low (at the selectivity ~80% only). The prepared catalysts may have some use in blends with more crystalline catalysts to control/reduce the amount of crystallization in the catalyst.

Example 2

Figure 4:
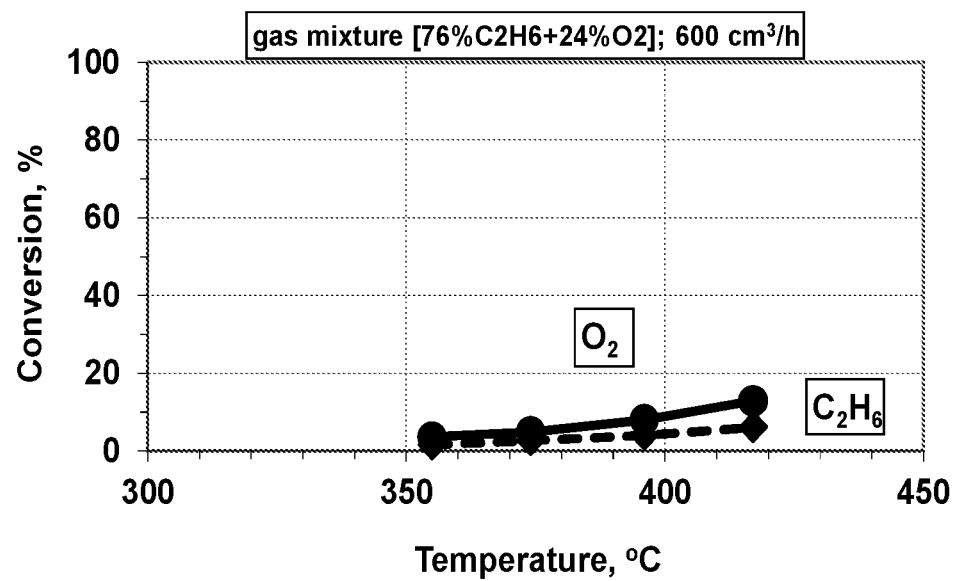
FIG. 4 is a plot of the conversion of the catalyst of Example 2.
Figure 5:
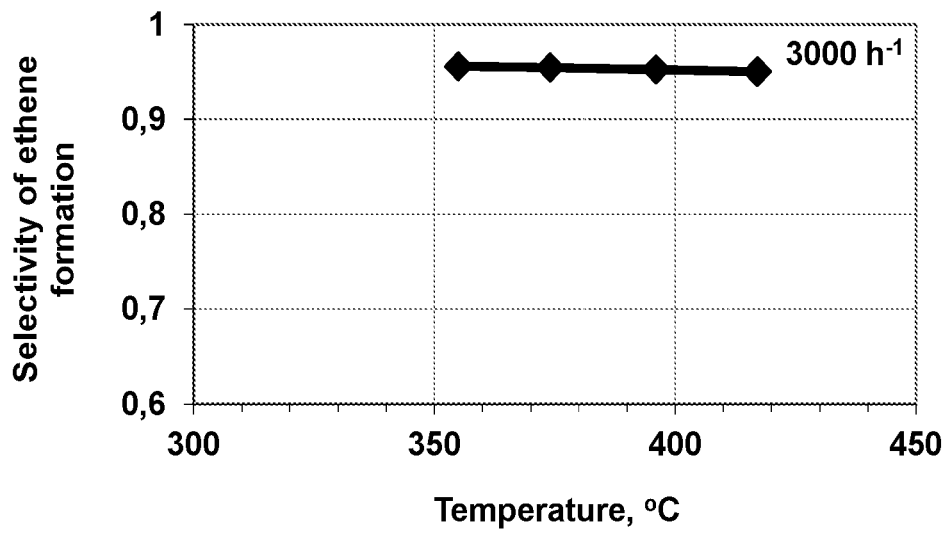
FIG. 5 is a plot of the selectivity of the catalyst of Example 2.
Figure 6:
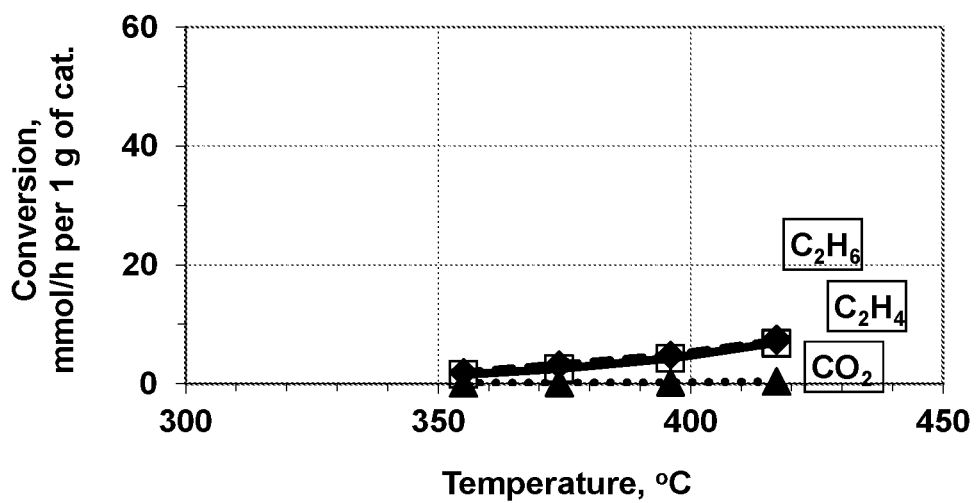
FIG. 6 is a plot of the conversion per mmol of catalyst of Example 2.

A catalyst of the formula $Mo_1V_{0.3}Te_{0.08}Nb_{0.12}O_X$ containing about half the usual amount of Te was prepared and tested for conversion of feed (oxygen and ethane), selectivity to ethylene and selectivity of ethane to ethylene per mmol/per hour gram of catalyst (productivity). The conversion is plotted in FIG. 4, the selectivity is plotted in FIG. 5, and the conversion per mmol of catalyst is plotted in FIG. 6.

The conversion of feed was low but the selectivity to ethylene was excellent.

Example 3

Figure 7:
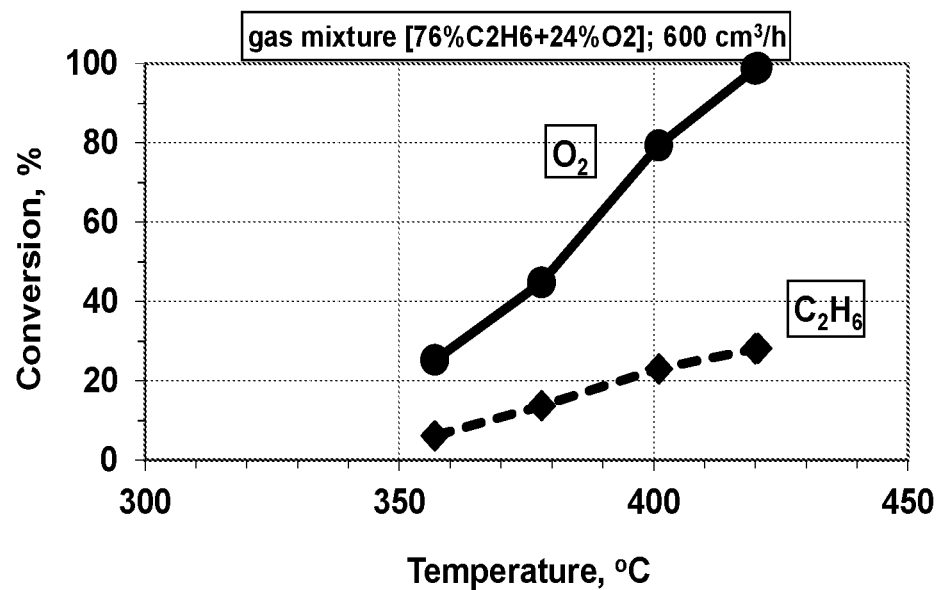
FIG. 7 is a plot of the conversion of the catalyst of Example 3.
Figure 8:
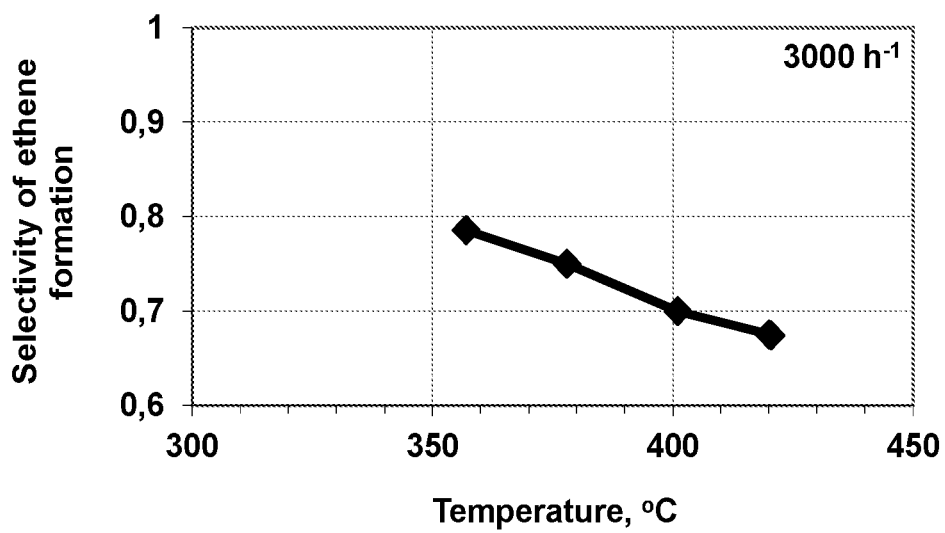
FIG. 8 is a plot of the selectivity of the catalyst of Example 3.
Figure 9:
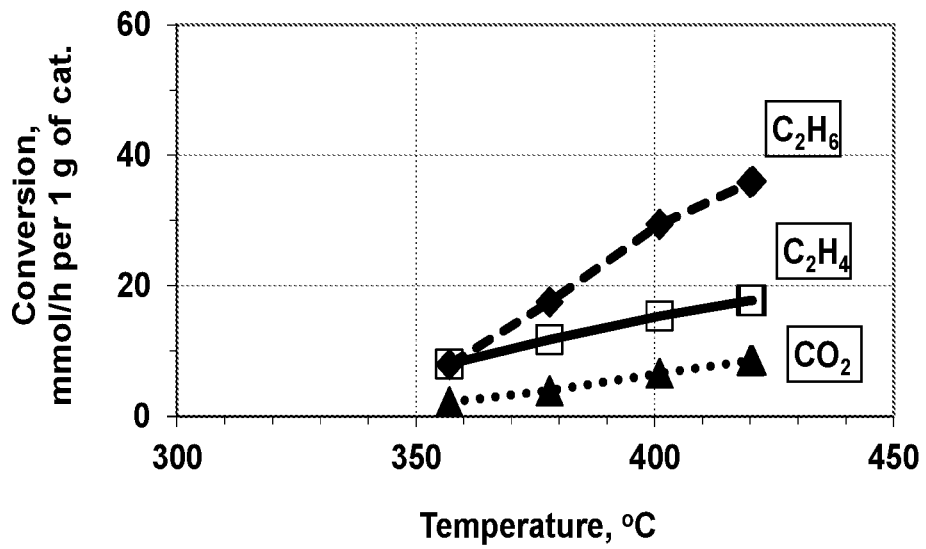
FIG. 9 is a plot of the conversion per mmol of catalyst of Example 3.

A catalyst was prepared with complete substitution of Mo by W. The catalyst had the formula: $W_1V_{0.3}Te_{0.08}Nb_{0.12}O_X$. The catalyst was tested as above. The conversion is plotted in FIG. 7, the selectivity is plotted in FIG. 8, and the conversion per mmol of catalyst is plotted in FIG. 9. The conversion of ethane is low below temperatures of about 400° C. and conversion and selectivity to ethylene in the range from 350° C. to 450° C. are antagonistic in that as the conversion goes up the selectivity goes down. This is a poor candidate.

Example 4

A catalyst was prepared substituting half of the Te with W. The duplicate catalyst samples were prepared in one case using $H_2WO_4$ or ammonium meta-tungstate as the source of W. Both catalysts acted in substantially similar manners.

Figure 10:
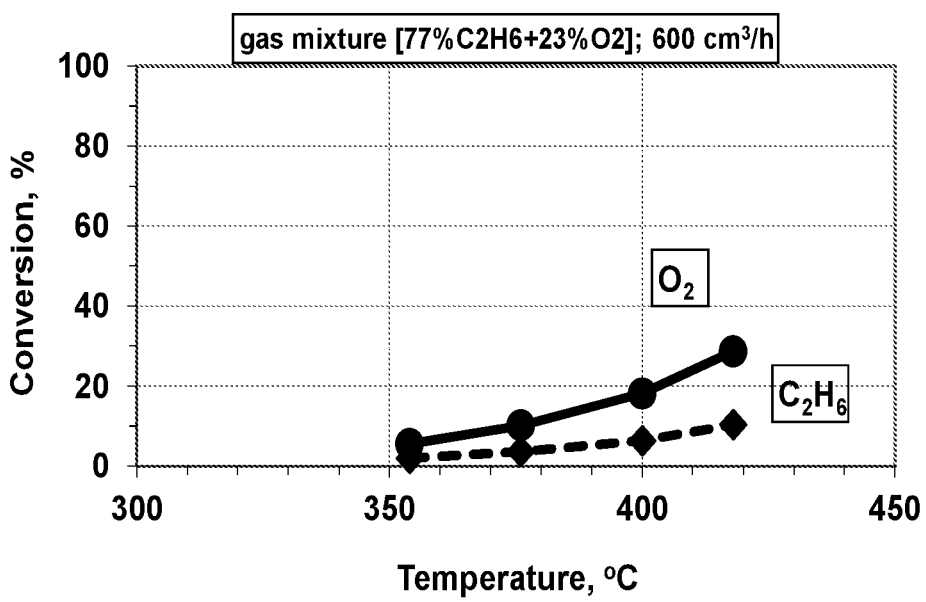
FIG. 10 is a plot of the conversion of the catalyst of Example 4.
Figure 11:
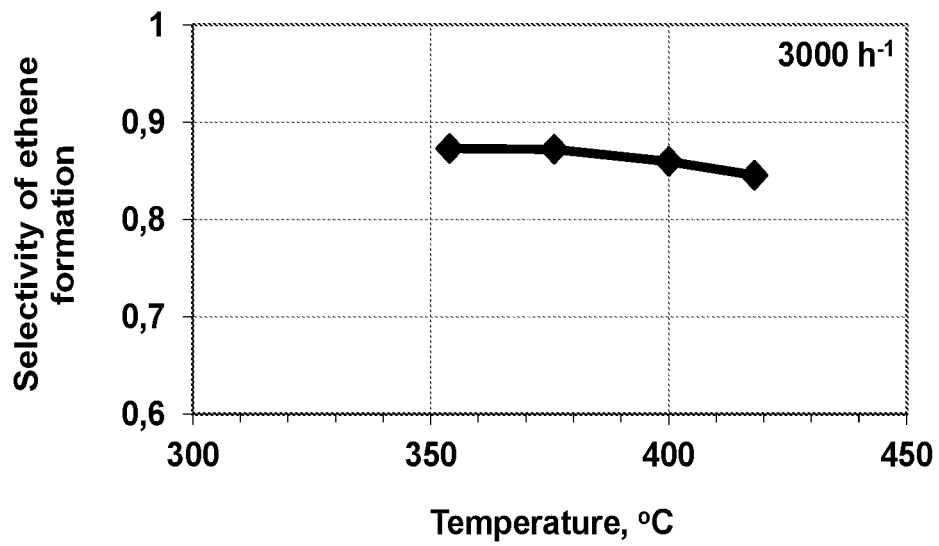
FIG. 11 is a plot of the selectivity of the catalyst of Example 4.
Figure 12:
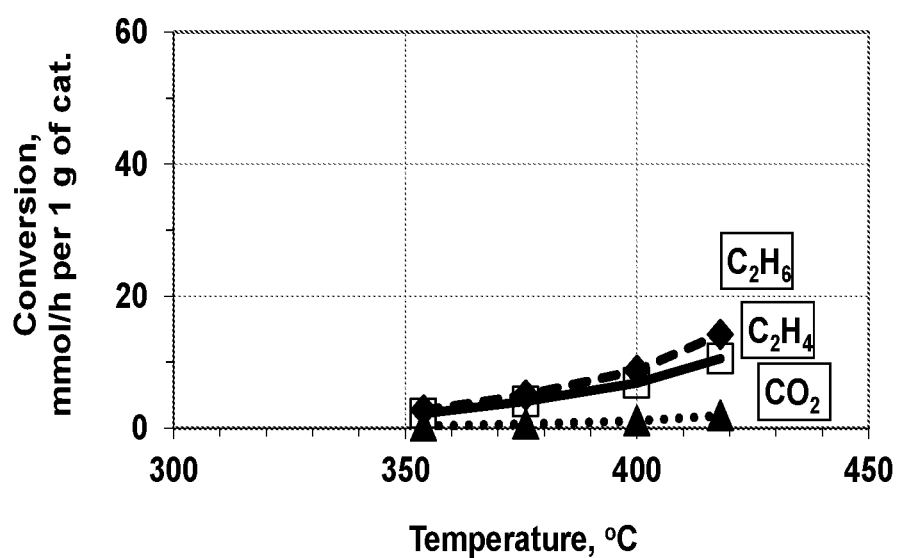
FIG. 12 is a plot of the conversion per mmol of catalyst of Example 4.

The catalyst had the formula: $Mo_1V_{0.3}Te_{0.07}W_{0.07}Nb_{0.11}O_X$. The results for the catalyst prepared using $H_2WO_4$ was tested for as above. The conversion is plotted in FIG. 10, the selectivity is plotted in FIG. 11, and the conversion per mmol of catalyst is plotted in FIG. 12. While the selectivity is reasonable the conversion of ethane to products is low.

Example 5

Figure 13:
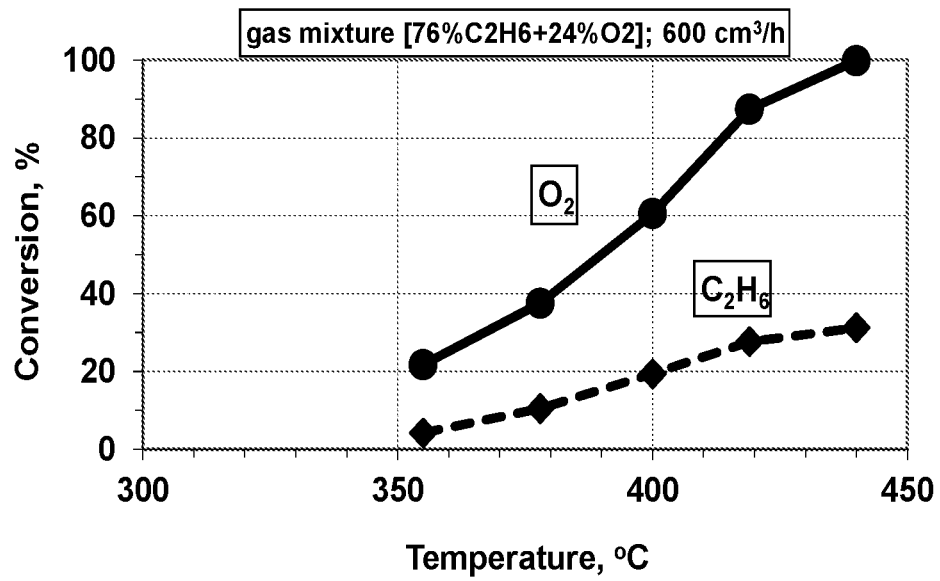
FIG. 13 is a plot of the conversion of the catalyst of Example 5.
Figure 14:
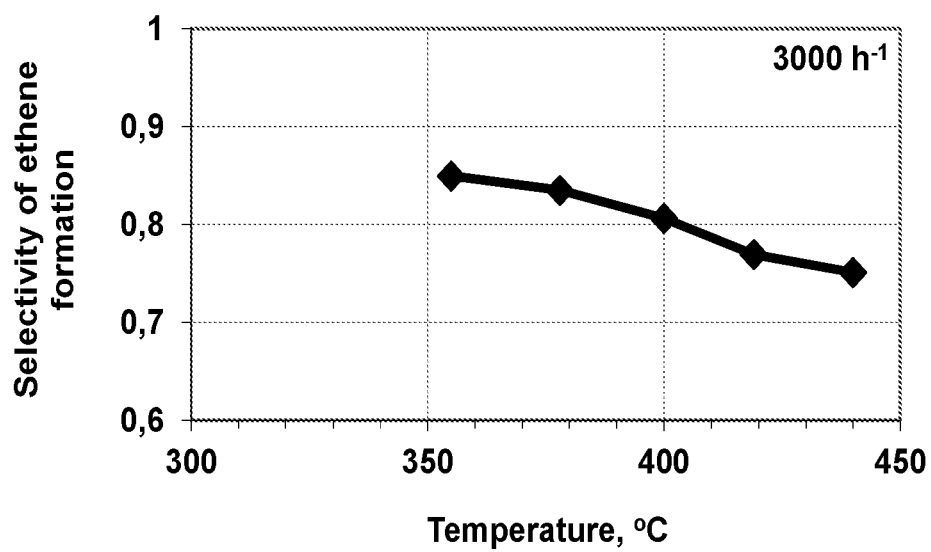
FIG. 14 is a plot of the selectivity of the catalyst of Example 5.
Figure 15:
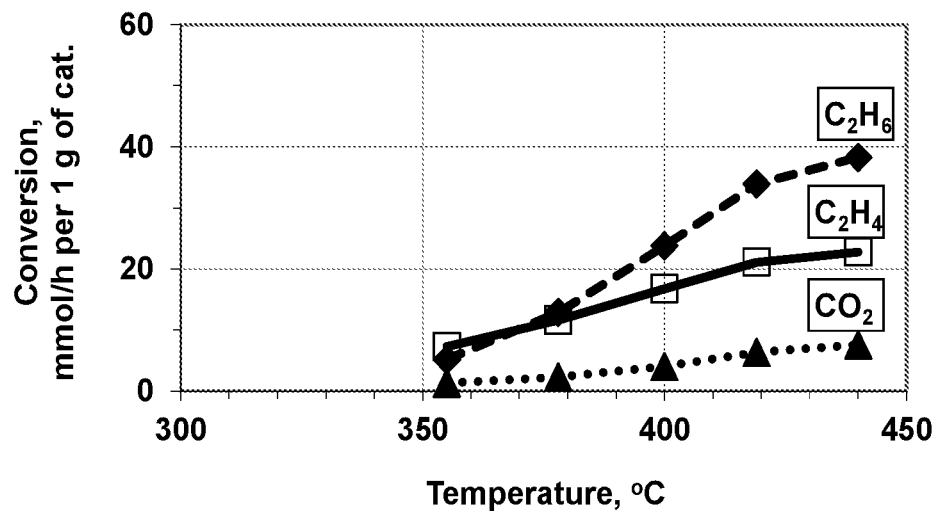
FIG. 15 is a plot of the conversion per mmol of catalyst of Example 5.

A catalyst was prepared with complete substitution of Mo by W, and partial substitution of Te with Fe. The catalyst had the formula:. $W_1V_{0.3}Te_{0.08}Fe_{0.08}Nb_{0.12}O_X$. The catalyst was tested for as above. The conversion is plotted in FIG. 13, the selectivity is plotted in FIG. 14, and the conversion per mmol of catalyst is plotted in FIG. 15. While there is some loss of ethane to $CO_2$ at temperatures below about 430° C., the catalyst has the potential for commercial use.

Example 6

Figure 17:
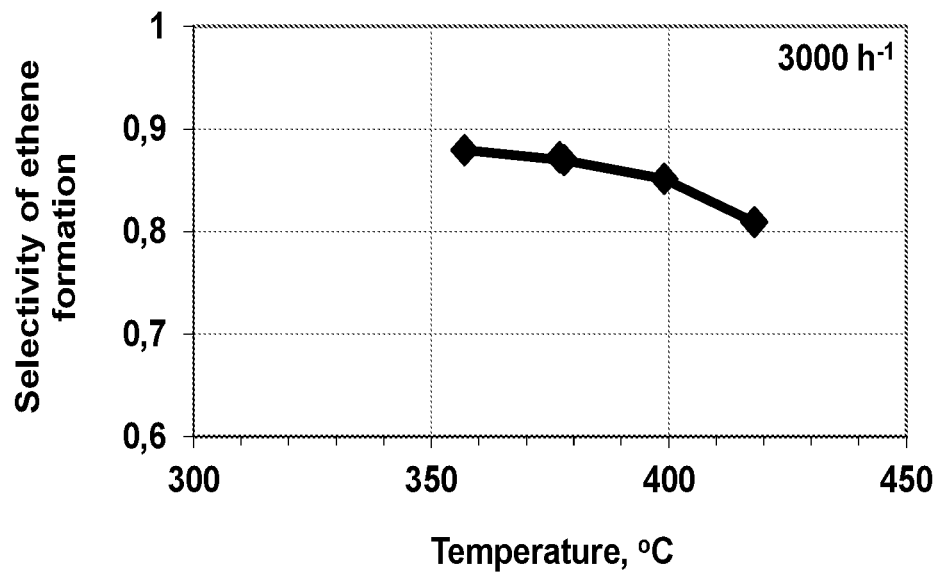
FIG. 17 is a plot of the selectivity of the catalyst of Example 6.
Figure 18:
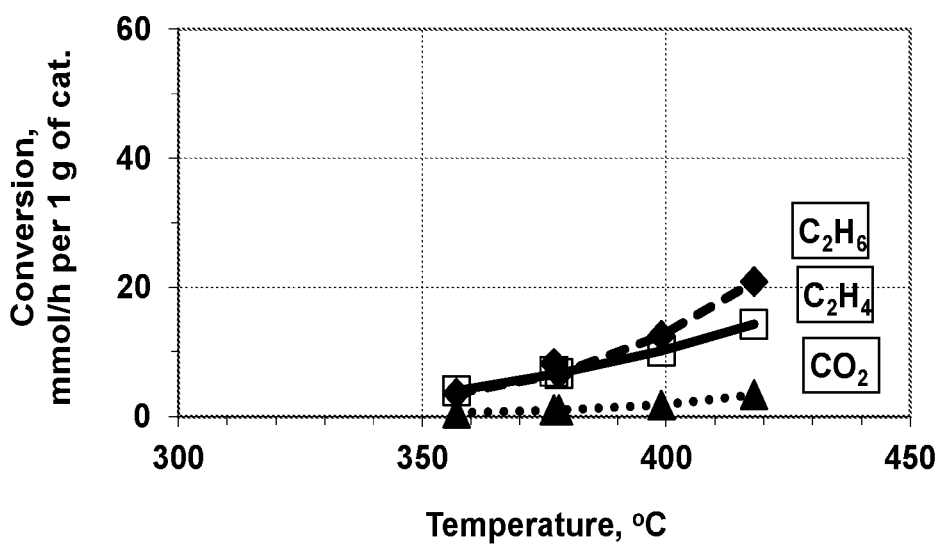
FIG. 18 is a plot of the conversion per mmol of catalyst of Example 6.

A catalyst was prepared with complete substitution of Mo by W. The catalyst had the formula: $W_1V_{0.3}Te_{0.16}Nb_{0.12}O_X$. The catalyst was tested for as above. The conversion is plotted in FIG. 16, the selectivity is plotted in FIG. 17, and the conversion per mmol of catalyst is plotted in FIG. 18. While there is some loss of ethane to $CO_2$ at temperatures below about 430° C., the catalyst has the potential for commercial use.

Example 7

Figure 19:
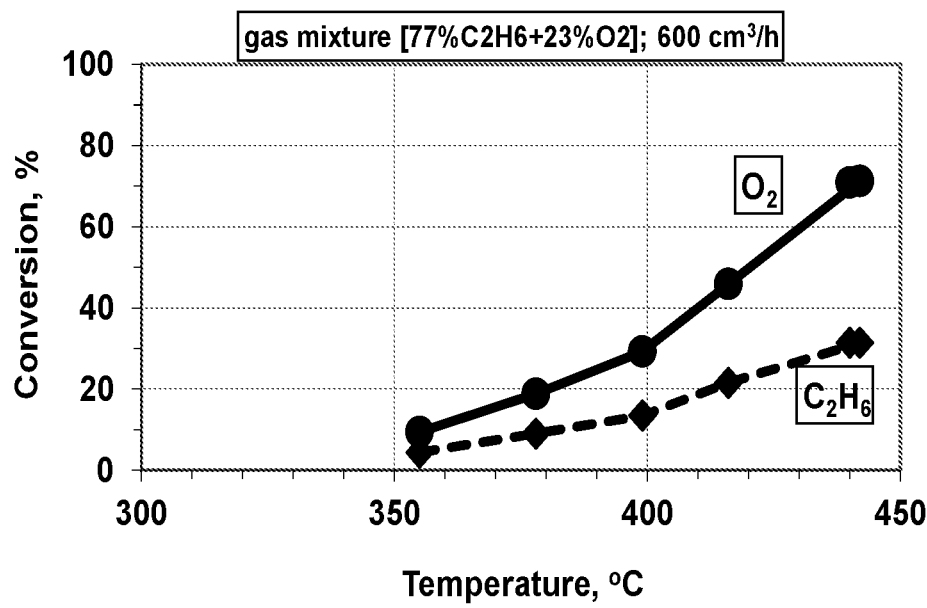
FIG. 19 is a plot of the conversion of the catalyst of Example 7.
Figure 20:
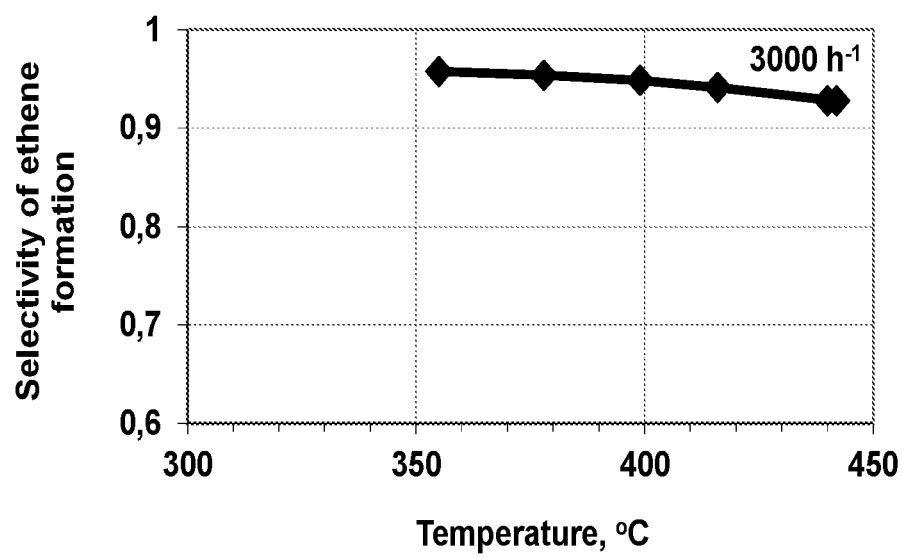
FIG. 20 is a plot of the selectivity of the catalyst of Example 7.
Figure 21:
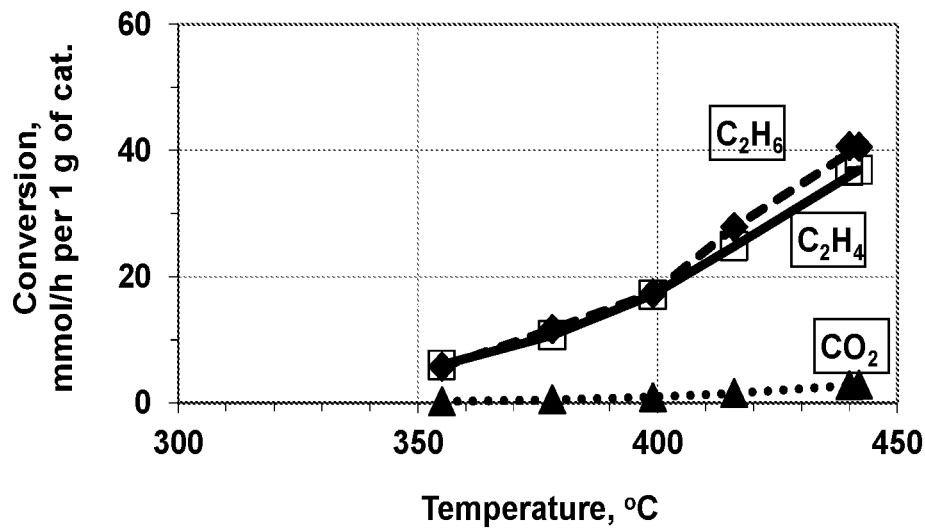
FIG. 21 is a plot of the conversion per mmol of catalyst of Example 7.

A sample was prepared as above with half of the Te substituted by Fe. The formula of the catalyst was $Mo_1V_{0.3}Te_{0.06}Fe_{0.06}Nb_{0.11}O_X$ where X meets the oxidation state of the mixed oxide. The catalyst was tested for as above. The conversion is plotted in FIG. 19, the selectivity is plotted in FIG. 20, and the conversion per mmol of catalyst is plotted in FIG. 21.

Based on the above examples, catalysts of the formula: $Mo_{0-1}W_{0.3-1}V_{0.2-0.4}Te_{0.06-0.10}Fe_{0.0-0.10}Nb_{0.08-0.18}O_X$, where X is determined by the valance of the metal oxides, have reasonable conversion of feeds, selectivity to ethylene and conversion in terms of mmol of feed per hour per gram of catalysts, over a temperature range from 325° C. to 425° C., and can be useful in the commercial oxidative dehydrogenation of ethane to ethylene.

Comparative Examples

Comparative 1

Figure 22:
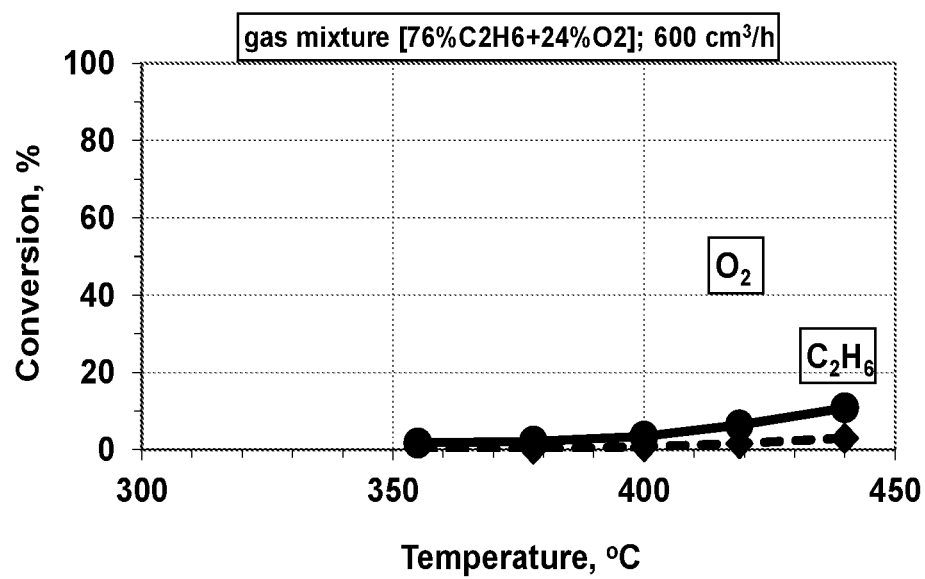
FIG. 22 is a plot of the conversion using air calcined catalyst of Comparative Example 1.

A sample of the catalyst precursor of Example 6 above was calcined in air. The conversion feed using the air calcined catalyst is shown in FIG. 22. The catalyst has an extremely low conversion and is not suitable for industrial use.

Comparative 2

Figure 23:
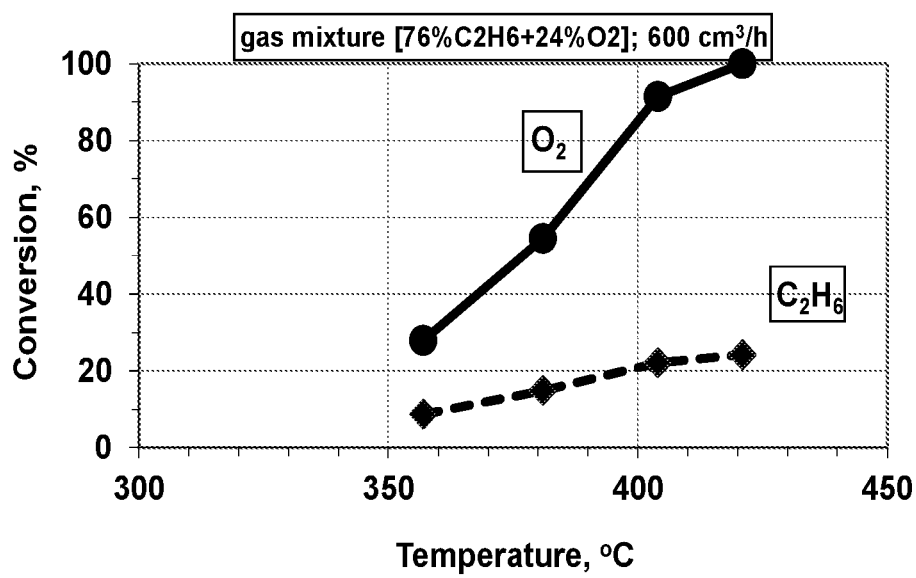
FIG. 23 is a plot of the conversion of the catalyst of Comparative Example 2.
Figure 24:
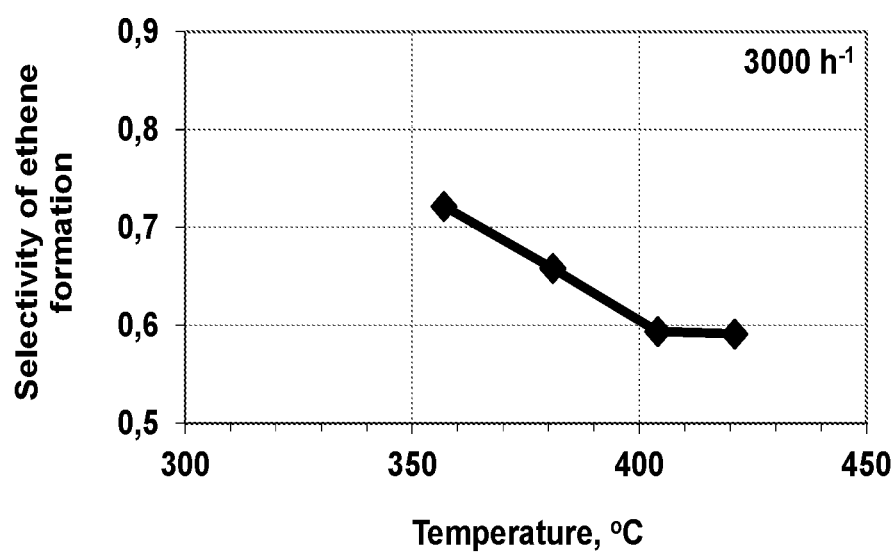
FIG. 24 is a plot of the selectivity curve for the catalyst at a flow rate of 3000 hr$^{-1}$ of Comparative Example 2.

A catalyst sample of the formula $W_1V_{0.3}Fe_{0.16}Nb_{0.12}O_X$ was prepared as tested as above and calcined under $N_2$ at 600° C. FIG. 23 shows the conversion and FIG. 24 shows the selectivity curve for the catalyst at a flow rate of 3000 $hr^{-1}$. The curves are antagonistic. The conversion (%) is low at low temperatures and the selectivity falls at higher temperatures. The catalyst appears to be burning feedstock at these conditions.

Comparative 3

Figure 16:
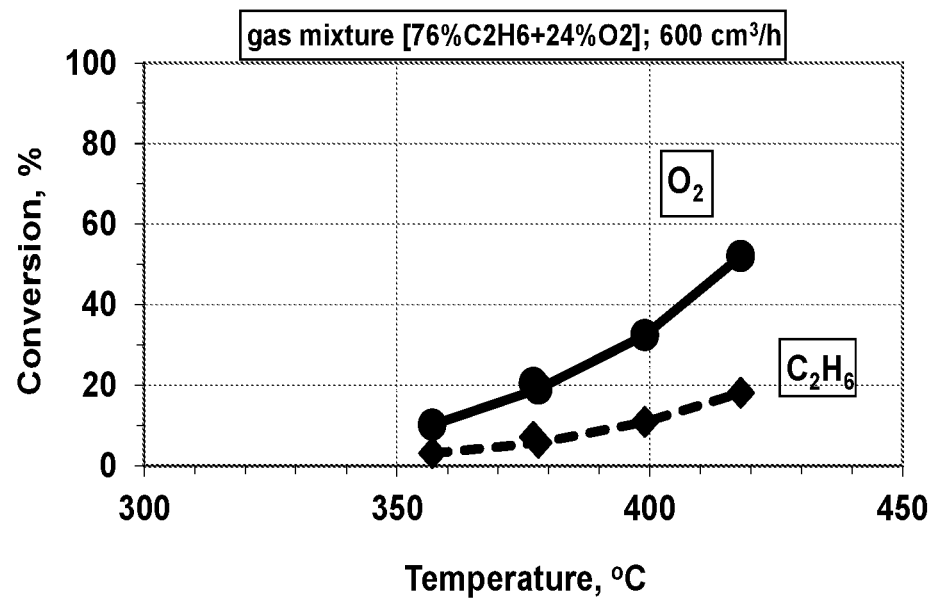
FIG. 16 is a plot of the conversion of the catalyst of Example 6.
Figure 25:
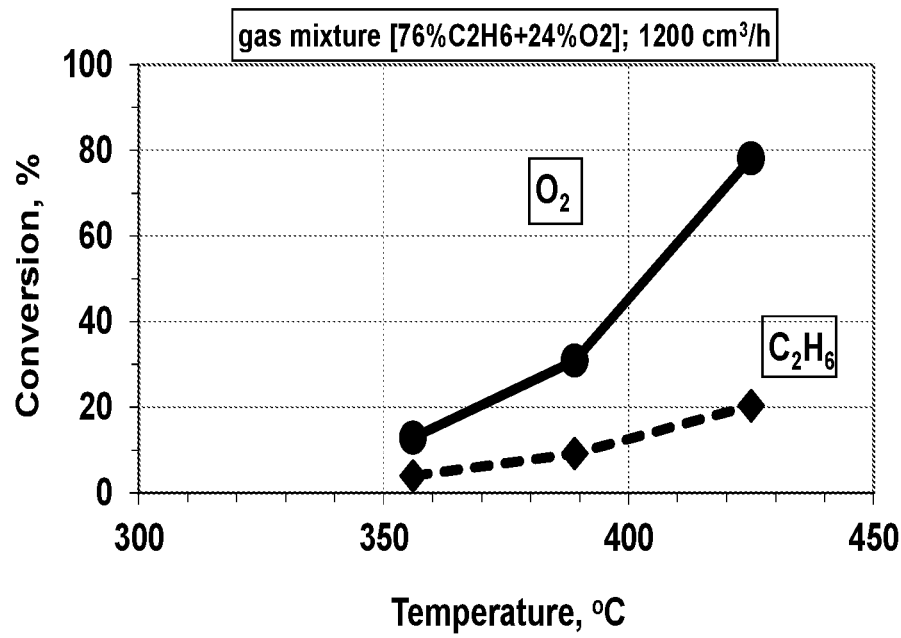
FIG. 25 is a plot of the conversion of the catalyst of Comparative Example 3.
Figure 26:
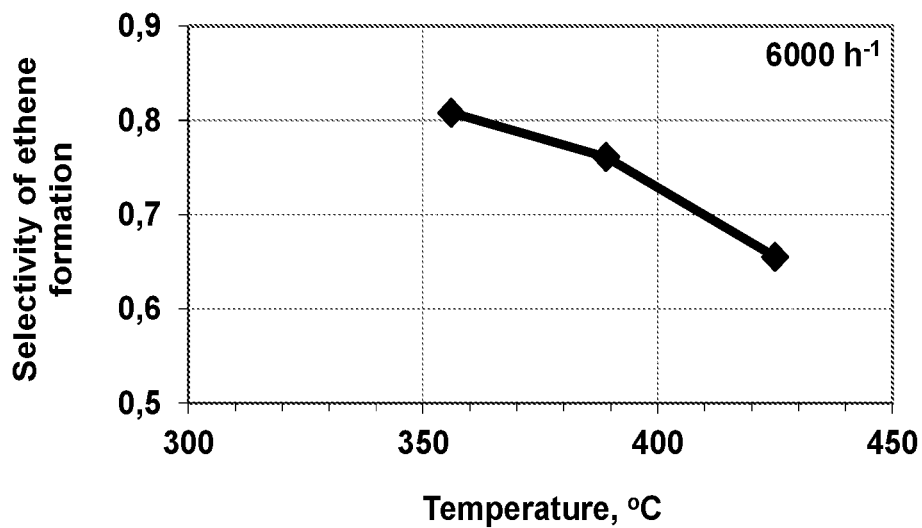
FIG. 26 is a plot of the selectivity of the catalyst of Comparative Example 3.

Comparative Example 2 was repeated at a flow rate of 6000 $hr^{-1}$. FIG. 25 shows the conversion and FIG. 16 shows the selectivity curve. The shape of the selectivity curve has improved somewhat but it does not overcome the poor productivity curve.

Comparative 4

Figure 27:
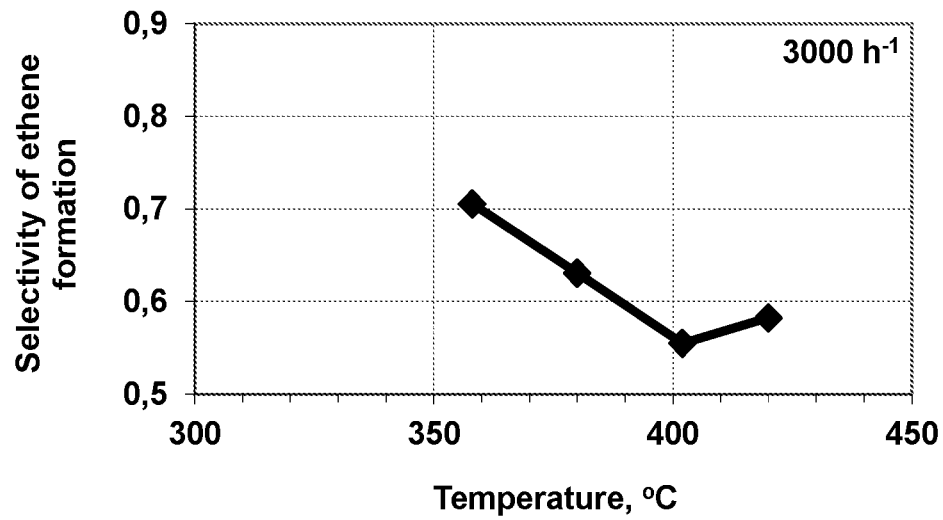
FIG. 27 is a plot of the selectivity of the catalyst washed with $H_2O_2$ of Comparative Example 4.

Comparative Example 2 was repeated but the catalyst was washed with $H_2O_2$. FIG. 27 shows that the selectivity went down.

Comparative 5

Figure 28:
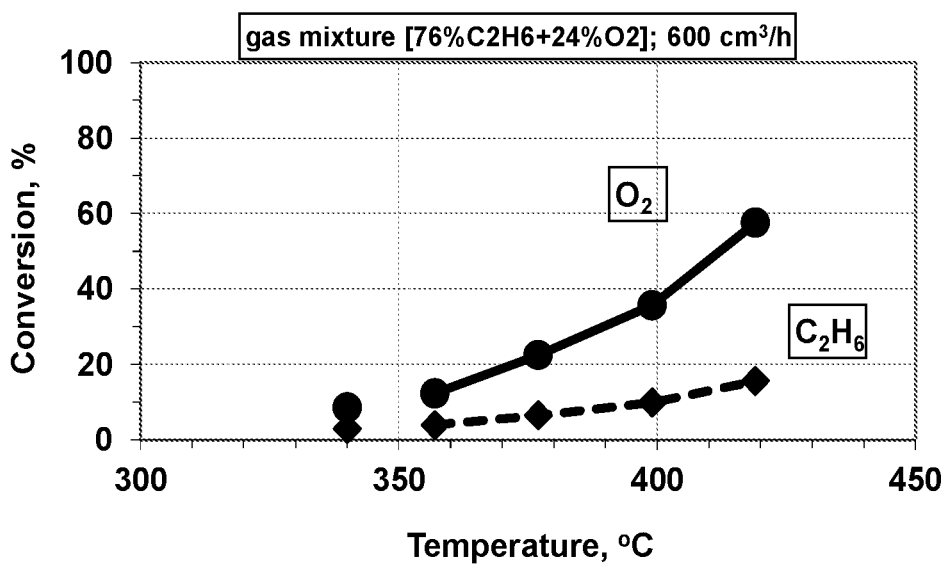
FIG. 28 is a plot of the conversion of the catalyst of Comparative Example 5.
Figure 29:
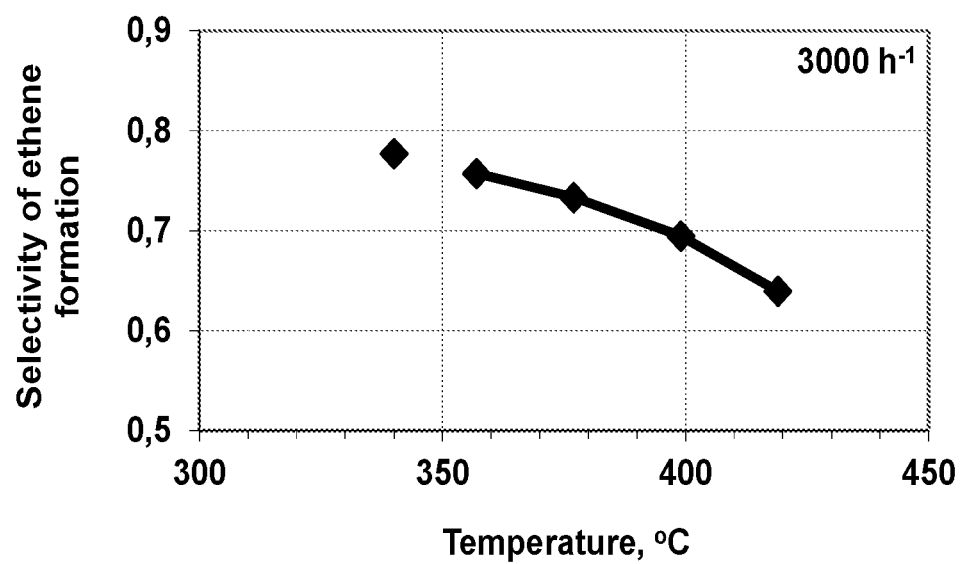
FIG. 29 is a plot of the selectivity of the catalyst of Comparative Example 5.

A catalyst of the formula $W_1V_{0.3}Sb_{0.16}Nb_{0.12}O_X$ was prepared and tested. The selectivity was low and the conversion was low. The conversion is plotted in FIG. 28, the selectivity is plotted in FIG. 29.

INDUSTRIAL APPLICABILITY

This disclosure relates to catalysts for the oxidative dehydrogenation of ethane to ethylene.

The invention claimed is:

1. A catalyst comprising $Mo_{0-1}W_{0.3-1}V_{0.2-0.4}Te_{0.06-0.10}Fe_{0.0-0.10}Nb_{0.08-0.18}Ox$ where X is determined by the valence of the metals, wherein the catalyst comprises Mo.

2. The catalyst according to claim 1, wherein the catalyst comprises $MO_{0.3-0.8}W_{0.3-0.8}V_{0.2-0.4}Te_{0.06-0.10}Fe_{0.06-0.10}Nb_{0.08-0.14}Ox$ where X is determined by the valence of the metals.

3. The catalyst according to claim 2, wherein the catalyst has a conversion from 65% to 90% for the oxidative dehydrogenation of ethane to ethylene at temperatures from 300° C. to 450° C.

4. The catalyst according to claim 2, wherein the catalyst has a conversion from 65% to 85% for the oxidative dehydrogenation of ethane to ethylene at temperatures from 350° C. to 425° C.

5. The catalyst according to claim 1, wherein the catalyst comprises $MO_{0.45-0.55}W_{0.45-0.55}V_{0.25-0.35}Te_{0.07-0.09}Fe_{0.07-0.09}Nb_{0.11-0.13}Ox$ where X is determined by the valence of the metals.

6. The catalyst according to claim 1, wherein the catalyst comprises $MO_{0.48-0.52}W_{0.48-0.52}V_{0.28-0.32}Te_{0.075-0.085}Fe_{0.075-0.085}Nb_{0.115-0.125}Ox$ where X is determined by the valence of the metals.

7. The catalyst according to claim 1, wherein the catalyst has a conversion from 65% to 90% for the oxidative dehydrogenation of ethane to ethylene at temperatures from 300° ° C. to 450° C.

8. The catalyst according to claim 1, wherein the catalyst has a conversion from 65% to 85% for the oxidative dehydrogenation of ethane to ethylene at temperatures from 350° C. to 425° C.

9. An article, comprising:
a support; and
a catalyst supported by the support,
wherein:
the support comprises at least one member selected from the group consisting of oxides of titanium, zirconia, aluminum, niobium, magnesium, yttrium, lanthanum, or silicon, zeolites and clays;
the catalyst comprises $Mo_{0-1}W_{0.3-1}V_{0.2-0.4}Te_{0.06-0.10}Fe_{0.0-0.10}Nb_{0.08-0.18}Ox$ where X is determined by the valence of the metals; and
the catalyst comprises Mo.

10. The article according to claim 9, wherein the catalyst comprises $Mo_{0.3-0.8}W_{0.3-0.8}V_{0.2-0.4}Te_{0.06-0.10}Fe_{0.06-0.10}Nb_{0.08-0.14}Ox$ where X is determined by the valence of the metals.

11. The article according to claim 9, wherein the catalyst comprises $Mo_{0.45-0.55}W_{0.45-0.55}V_{0.25-0.35}Te_{0.07-0.09}Fe_{0.07-0.09}Nb_{0.11-0.13}Ox$ where X is determined by the valence the metals.

12. The article according to claim 9, wherein the catalyst comprises $Mo_{0.48-0.52}W_{0.48-0.52}V_{0.28-0.32}Te_{0.075-0.085}Fe_{0.075-0.085}Nb_{0.115-0.125}Ox$ where X is determined by the valence of the metals.

13. The article according to claim 9, wherein the catalyst has a conversion from 65% to 90% for the oxidative dehydrogenation of ethane to ethylene at temperatures from 300° C. to 450° C.

14. The article according to claim 9, wherein the catalyst has a conversion from 65% to 85% for the oxidative dehydrogenation of ethane to ethylene at temperatures from 350° C. to 425° C.

15. A method, comprising:
contacting ethane and an oxidant with a catalyst to provide ethylene,
wherein the catalyst comprises $Mo_{0-1}W_{0.3-1}V_{0.2-0.4}Te_{0.06-0.10}Fe_{0.0-0.10}Nb_{0.08-0.18}Ox$ where X is determined by the valence of the metals, and the catalyst comprises Mo.

16. The method of claim 15, wherein the catalyst comprises $MO_{0.3-0.8}W_{0.3-0.8}V_{0.2-0.4}Te_{0.06-0.10}Fe_{0.06-0.10}Nb_{0.08-0.14}Ox$ where X is determined by the valence of the metals.

17. The method of claim 15, wherein the catalyst comprises $Mo_{0.45-0.55}W_{0.45-0.55}V_{0.25-0.35}Te_{0.07-0.09}Fe_{0.07-0.09}Nb_{0.11-0.13}Ox$ where X is determined by the valence the metals.

18. The method of claim 15, wherein the catalyst comprises $Mo_{0.48-0.52}W_{0.48-0.52}V_{0.28-0.32}Te_{0.075-0.085}Fe_{0.075-0.085}Nb_{0.115-0.125}Ox$ where X is determined by the valence of the metals.

19. The method of claim 15, wherein the catalyst has a conversion from 65% to 90% for converting ethane to ethylene at temperatures from 300° ° C. to 450° C.

20. The method of claim 15, wherein the catalyst has a conversion from 65% to 85% for converting ethane to ethylene at temperatures from 350° C. to 425° C.

* * * * *

UNITED STATES PATENT AND TRADEMARK OFFICE
CERTIFICATE OF CORRECTION

Page 1 of 2

PATENT NO. : 12,128,386 B2
APPLICATION NO. : 17/621001
DATED : October 29, 2024
INVENTOR(S) : Xiaoliang Gao et al.

It is certified that error appears in the above-identified patent and that said Letters Patent is hereby corrected as shown below:

On the Title Page

Column 2, Line 11, (57) Abstract, please replace "valance" with -- valence --.

In the Claims

Column 14, Line 29, Claim 2, please replace "$MO_{0.3-0.8}$" with -- $Mo_{0.3-0.8}$ --.

In Column 14, Line 41, Claim 5, please replace "$MO_{0.45-0.55}$" with -- $Mo_{0.45-0.55}$ --.

In Column 14, Line 42, Claim 5, please replace "Ox" with -- $O_x$ --.

In Column 14, Line 45, Claim 6, please replace "$MO_{0.48-0.52}$" with -- $Mo_{0.48-0.52}$ --.

In Column 14, Line 46, Claim 6, please replace "Ox" with -- $O_x$ --.

In Column 14, Line 51, Claim 7, please replace "300° ° C." with -- 300° C. --.

In Column 15, Line 7, Claim 11, please replace "Ox" with -- $O_x$ --.

In Column 15, Line 8, Claim 11, please replace "valence" with -- valence of --.

In Column 15, Line 11, Claim 12, please replace "Ox" with -- $O_x$ --.

In Column 16, Line 6, Claim 16, please replace ""$MO_{0.3-0.8}$" with -- $Mo_{0.3-0.8}$ --.

In Column 16, Line 11, Claim 17, please replace "Ox" with -- $O_x$ --.

In Column 16, Line 12, Claim 17, please replace "valence" with -- valence of --.

Signed and Sealed this
Seventeenth Day of December, 2024

Derrick Brent
*Acting Director of the United States Patent and Trademark Office*

In Column 16, Line 15, Claim 18, please replace "Ox" with -- $O_x$ --.

In Column 16, Line 19, Claim 19, please replace "300° ° C." with -- 300° C. --.